(12) United States Patent
Andrews et al.

(10) Patent No.: US 11,576,562 B2
(45) Date of Patent: Feb. 14, 2023

(54) CAMERA POSITIONING METHOD AND APPARATUS FOR CAPTURING IMAGES DURING A MEDICAL PROCEDURE

(71) Applicant: Titan Medical Inc., Toronto (CA)

(72) Inventors: Richard Andrews, North Attleboro, MA (US); Leonard M. Faria, Swansea, MA (US)

(73) Assignee: TITAN MEDICAL INC., Toronto (CA)

( * ) Notice: Subject to any disclaimer, the term of this patent is extended or adjusted under 35 U.S.C. 154(b) by 270 days.

(21) Appl. No.: 16/085,152

(22) PCT Filed: Apr. 4, 2017

(86) PCT No.: PCT/CA2017/000078
§ 371 (c)(1),
(2) Date: Sep. 14, 2018

(87) PCT Pub. No.: WO2017/173524
PCT Pub. Date: Oct. 12, 2017

(65) Prior Publication Data
US 2019/0082931 A1  Mar. 21, 2019

Related U.S. Application Data

(60) Provisional application No. 62/319,426, filed on Apr. 7, 2016.

(51) Int. Cl.
*A61B 1/008* (2006.01)
*A61B 1/01* (2006.01)
(Continued)

(52) U.S. Cl.
CPC .......... *A61B 1/008* (2013.01); *A61B 1/00096* (2013.01); *A61B 1/01* (2013.01);
(Continued)

(58) Field of Classification Search
CPC ....... A61B 1/008; A61B 1/06; A61B 1/00096; A61B 1/0661; A61B 1/01; A61B 1/05; A61B 34/00; A61B 18/00; A61B 17/00
(Continued)

(56) References Cited

U.S. PATENT DOCUMENTS 6,007,484 A * 12/1999 Thompson ......... A61B 1/00096
600/122
6,132,368 A 10/2000 Cooper
(Continued)

FOREIGN PATENT DOCUMENTS

| CA | 2913943 A1 * 12/2014 | ........... A61B 1/0055 |
| JP | 2013246385 A * 12/2013 | |
| WO | WO-2015161249 A1 * 10/2015 | ..... A61B 17/320016 |

OTHER PUBLICATIONS

International Search Report and Written Opinion in International Application No. PCT/CA2017/000078, dated Aug. 17, 2017, in 10 pages.

*Primary Examiner* — Aaron B Fairchild
*Assistant Examiner* — Christen A. Sharpless
(74) *Attorney, Agent, or Firm* — Carter, DeLuca & Farrell, LLP (57) ABSTRACT

A method and apparatus for positioning a camera to capture images inside a body cavity of a patient during a medical procedure is disclosed. The apparatus includes an insertion tube, a plurality of connected linkages extending from a distal end of the insertion tube, each linkage having a threaded actuator received on a threaded end of a drive shaft extending between the threaded actuator and a proximal end of the insertion tube. The apparatus also includes a camera disposed at a distal end of the plurality of connected linkages. Each connected linkage has at least one associated movement actuated by movement of the threaded actuator in response to rotation of the drive shaft, the associated move- (Continued)

ments of the connected linkages together operable to facilitate positioning of the camera within the body cavity of the patient.

20 Claims, 4 Drawing Sheets (51) Int. Cl.
*A61B 1/05* (2006.01)
*A61B 1/06* (2006.01)
*A61B 1/00* (2006.01)

(52) U.S. Cl.
CPC .................. *A61B 1/05* (2013.01); *A61B 1/06* (2013.01); *A61B 1/0661* (2013.01)

(58) Field of Classification Search
USPC ........................................................ 600/141
See application file for complete search history.

(56) References Cited

U.S. PATENT DOCUMENTS

| | | |
|---|---|---|
| 6,206,903 B1 | 3/2001 | Ramans |
| 6,246,200 B1 | 6/2001 | Blumenkranz et al. |
| 6,312,435 B1 | 11/2001 | Wallace et al. |
| 6,331,181 B1 | 12/2001 | Tierney et al. |
| 6,394,998 B1 | 5/2002 | Wallace et al. |
| 6,424,885 B1 | 7/2002 | Niemeyer et al. |
| 6,441,577 B2 | 8/2002 | Blumenkranz et al. |
| 6,459,926 B1 | 10/2002 | Nowlin et al. |
| 6,491,691 B1 | 12/2002 | Morley et al. |
| 6,491,701 B2 | 12/2002 | Tierney et al. |
| 6,493,608 B1 | 12/2002 | Niemeyer |
| 6,565,554 B1 | 5/2003 | Niemeyer |
| 6,645,196 B1 | 11/2003 | Nixon et al. |
| 6,648,816 B2 | 11/2003 | Irion et al. |
| 6,659,939 B2 | 12/2003 | Moll et al. |
| 6,671,581 B2 | 12/2003 | Niemeyer et al. |
| 6,676,684 B1 | 1/2004 | Morley et al. |
| 6,685,698 B2 | 2/2004 | Morley et al. |
| 6,699,235 B2 | 3/2004 | Wallace et al. |
| 6,714,839 B2 | 3/2004 | Salisbury, Jr. et al. |
| 6,716,233 B1 | 4/2004 | Whitman |
| 6,728,599 B2 | 4/2004 | Wang et al. |
| 6,746,443 B1 | 6/2004 | Morley et al. |
| 6,766,204 B2 | 7/2004 | Niemeyer et al. |
| 6,770,081 B1 | 8/2004 | Cooper et al. |
| 6,772,053 B2 | 8/2004 | Niemeyer |
| 6,783,524 B2 | 8/2004 | Anderson et al. |
| 6,793,652 B1 | 9/2004 | Whitman et al. |
| 6,793,653 B2 | 9/2004 | Sanchez et al. |
| 6,799,065 B1 | 9/2004 | Niemeyer |
| 6,837,883 B2 | 1/2005 | Moll et al. |
| 6,839,612 B2 | 1/2005 | Sanchez et al. |
| 6,840,938 B1 | 1/2005 | Morley et al. |
| 6,843,403 B2 | 1/2005 | Whitman |
| 6,846,309 B2 | 1/2005 | Whitman et al. |
| 6,866,671 B2 | 3/2005 | Tierney et al. |
| 6,871,117 B2 | 3/2005 | Wang et al. |
| 6,879,880 B2 | 4/2005 | Nowlin et al. |
| 6,899,705 B2 | 5/2005 | Niemeyer |
| 6,902,560 B1 | 6/2005 | Morley et al. |
| 6,936,042 B2 | 8/2005 | Wallace et al. |
| 6,951,535 B2 | 10/2005 | Ghodoussi et al. |
| 6,974,449 B2 | 12/2005 | Niemeyer |
| 6,991,627 B2 | 1/2006 | Madhani et al. |
| 6,994,708 B2 | 2/2006 | Manzo |
| 7,048,745 B2 | 5/2006 | Tierney et al. |
| 7,066,926 B2 | 6/2006 | Wallace et al. |
| 7,118,582 B1 | 10/2006 | Wang et al. |
| 7,125,403 B2 | 10/2006 | Julian et al. |
| 7,155,315 B2 | 12/2006 | Niemeyer et al. |
| 7,239,940 B2 | 7/2007 | Wang et al. |
| 7,306,597 B2 | 12/2007 | Manzo |
| 7,357,774 B2 | 4/2008 | Cooper |
| 7,373,219 B2 | 5/2008 | Nowlin et al. |
| 7,379,790 B2 | 5/2008 | Toth et al. |
| 7,386,365 B2 | 6/2008 | Nixon |
| 7,391,173 B2 | 6/2008 | Schena |
| 7,398,707 B2 | 7/2008 | Morley et al. |
| 7,413,565 B2 | 8/2008 | Wang et al. |
| 7,453,227 B2 | 11/2008 | Prisco et al. |
| 7,524,320 B2 | 4/2009 | Tierney et al. |
| 7,574,250 B2 | 8/2009 | Niemeyer |
| 7,594,912 B2 | 9/2009 | Cooper et al. |
| 7,607,440 B2 | 10/2009 | Coste-Maniere et al. |
| 7,666,191 B2 | 2/2010 | Orban, III et al. |
| 7,682,357 B2 | 3/2010 | Ghodoussi et al. |
| 7,689,320 B2 | 3/2010 | Prisco et al. |
| 7,695,481 B2 | 4/2010 | Wang et al. |
| 7,695,485 B2 | 4/2010 | Whitman et al. |
| 7,699,855 B2 | 4/2010 | Anderson et al. |
| 7,713,263 B2 | 5/2010 | Niemeyer |
| 7,725,214 B2 | 5/2010 | Diolaiti |
| 7,727,244 B2 | 6/2010 | Orban, III et al. |
| 7,741,802 B2 | 6/2010 | Prisco et al. |
| 7,756,036 B2 | 7/2010 | Druke et al. |
| 7,757,028 B2 | 7/2010 | Druke et al. |
| 7,762,825 B2 | 7/2010 | Burbank et al. |
| 7,778,733 B2 | 8/2010 | Nowlin et al. |
| 7,803,151 B2 | 9/2010 | Whitman |
| 7,806,891 B2 | 10/2010 | Nowlin et al. |
| 7,819,859 B2 | 10/2010 | Prisco et al. |
| 7,819,885 B2 | 10/2010 | Cooper |
| 7,824,401 B2 | 11/2010 | Manzo et al. |
| 7,835,823 B2 | 11/2010 | Sillman et al. |
| 7,843,158 B2 | 11/2010 | Prisco |
| 7,865,266 B2 | 1/2011 | Moll et al. |
| 7,865,269 B2 | 1/2011 | Prisco et al. |
| 7,886,743 B2 | 2/2011 | Cooper et al. |
| 7,899,578 B2 | 3/2011 | Prisco et al. |
| 7,907,166 B2 | 3/2011 | Lamprecht et al. |
| 7,935,130 B2 | 5/2011 | Williams |
| 7,963,913 B2 | 6/2011 | Devengenzo et al. |
| 7,983,793 B2 | 7/2011 | Toth et al. |
| 8,002,767 B2 | 8/2011 | Sanchez et al. |
| 8,004,229 B2 | 8/2011 | Nowlin et al. |
| 8,012,170 B2 | 9/2011 | Whitman et al. |
| 8,054,752 B2 | 11/2011 | Druke et al. |
| 8,062,288 B2 | 11/2011 | Cooper et al. |
| 8,079,950 B2 | 12/2011 | Stern et al. |
| 8,100,133 B2 | 1/2012 | Mintz et al. |
| 8,108,072 B2 | 1/2012 | Zhao et al. |
| 8,120,301 B2 | 2/2012 | Goldberg et al. |
| 8,142,447 B2 | 3/2012 | Cooper et al. |
| 8,147,503 B2 | 4/2012 | Zhao et al. |
| 8,151,661 B2 | 4/2012 | Schena et al. |
| 8,155,479 B2 | 4/2012 | Hoffman et al. |
| 8,182,469 B2 | 5/2012 | Anderson et al. |
| 8,202,278 B2 | 6/2012 | Orban, III et al. |
| 8,206,406 B2 | 6/2012 | Orban, III |
| 8,210,413 B2 | 7/2012 | Whitman et al. |
| 8,216,250 B2 | 7/2012 | Orban, III et al. |
| 8,220,468 B2 | 7/2012 | Cooper et al. |
| 8,256,319 B2 | 9/2012 | Cooper et al. |
| 8,285,517 B2 | 10/2012 | Sillman et al. |
| 8,315,720 B2 | 11/2012 | Mohr et al. |
| 8,335,590 B2 | 12/2012 | Costa et al. |
| 8,347,757 B2 | 1/2013 | Duval |
| 8,374,723 B2 | 2/2013 | Zhao et al. |
| 8,418,073 B2 | 4/2013 | Mohr et al. |
| 8,419,717 B2 | 4/2013 | Diolaiti et al. |
| 8,423,182 B2 | 4/2013 | Robinson et al. |
| 8,452,447 B2 | 5/2013 | Nixon |
| 8,454,585 B2 | 6/2013 | Whitman |
| 8,499,992 B2 | 8/2013 | Whitman et al. |
| 8,508,173 B2 | 8/2013 | Goldberg et al. |
| 8,512,229 B2 | 8/2013 | Saadat et al. |
| 8,528,440 B2 | 9/2013 | Morley et al. |
| 8,529,582 B2 | 9/2013 | Devengenzo et al. |
| 8,540,748 B2 | 9/2013 | Murphy et al. |
| 8,551,116 B2 | 10/2013 | Julian et al. |
| 8,562,516 B2 | 10/2013 | Saadat et al. |

(56) References Cited

U.S. PATENT DOCUMENTS

| | | |
|---|---|---|
| 8,562,594 B2 | 10/2013 | Cooper et al. |
| 8,594,841 B2 | 11/2013 | Zhao et al. |
| 8,597,182 B2 | 12/2013 | Stein et al. |
| 8,597,280 B2 | 12/2013 | Cooper et al. |
| 8,600,551 B2 | 12/2013 | Itkowitz et al. |
| 8,608,773 B2 | 12/2013 | Tierney et al. |
| 8,620,473 B2 | 12/2013 | Diolaiti et al. |
| 8,624,537 B2 | 1/2014 | Nowlin et al. |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,644,988 B2 | 2/2014 | Prisco et al. |
| 8,666,544 B2 | 3/2014 | Moll et al. |
| 8,668,638 B2 | 3/2014 | Donhowe et al. |
| 8,740,885 B2 | 6/2014 | Larkin et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,758,352 B2 | 6/2014 | Cooper et al. |
| 8,761,930 B2 | 6/2014 | Nixon |
| 8,768,516 B2 | 7/2014 | Diolaiti et al. |
| 8,786,241 B2 | 7/2014 | Nowlin et al. |
| 8,790,243 B2 | 7/2014 | Cooper et al. |
| 8,808,164 B2 | 8/2014 | Hoffman et al. |
| 8,816,628 B2 | 8/2014 | Nowlin et al. |
| 8,821,480 B2 | 9/2014 | Burbank |
| 8,823,308 B2 | 9/2014 | Nowlin et al. |
| 8,827,989 B2 | 9/2014 | Niemeyer |
| 8,838,270 B2 | 9/2014 | Druke et al. |
| 8,852,174 B2 | 10/2014 | Burbank |
| 8,858,547 B2 | 10/2014 | Brogna |
| 8,862,268 B2 | 10/2014 | Robinson et al. |
| 8,864,751 B2 | 10/2014 | Prisco et al. |
| 8,864,752 B2 | 10/2014 | Diolaiti et al. |
| 8,903,546 B2 | 12/2014 | Diolaiti et al. |
| 8,903,549 B2 | 12/2014 | Itkowitz et al. |
| 8,911,428 B2 | 12/2014 | Cooper et al. |
| 8,912,746 B2 | 12/2014 | Reid et al. |
| 8,944,070 B2 | 2/2015 | Guthart et al. |
| 8,989,903 B2 | 3/2015 | Weir et al. |
| 9,002,518 B2 | 4/2015 | Manzo et al. |
| 9,014,856 B2 | 4/2015 | Manzo et al. |
| 9,016,540 B2 | 4/2015 | Whitman et al. |
| 9,019,345 B2 | 4/2015 | O'Grady et al. |
| 9,028,478 B2 | 5/2015 | Mueller |
| 9,043,027 B2 | 5/2015 | Durant et al. |
| 9,050,120 B2 | 6/2015 | Swarup et al. |
| 9,055,961 B2 | 6/2015 | Manzo et al. |
| 9,068,628 B2 | 6/2015 | Solomon et al. |
| 9,078,684 B2 | 7/2015 | Williams |
| 9,084,623 B2 | 7/2015 | Gomez et al. |
| 9,095,362 B2 | 8/2015 | Dachs, II et al. |
| 9,096,033 B2 | 8/2015 | Holop et al. |
| 9,101,381 B2 | 8/2015 | Burbank et al. |
| 9,113,877 B1 | 8/2015 | Whitman et al. |
| 9,138,284 B2 | 9/2015 | Krom et al. |
| 9,144,456 B2 | 9/2015 | Rosa et al. |
| 9,198,730 B2 | 12/2015 | Prisco et al. |
| 9,204,923 B2 | 12/2015 | Manzo et al. |
| 9,226,648 B2 | 1/2016 | Saadat et al. |
| 9,226,750 B2 | 1/2016 | Weir et al. |
| 9,226,761 B2 | 1/2016 | Burbank |
| 9,232,984 B2 | 1/2016 | Guthart et al. |
| 9,241,766 B2 | 1/2016 | Duque et al. |
| 9,241,767 B2 | 1/2016 | Prisco et al. |
| 9,241,769 B2 | 1/2016 | Larkin et al. |
| 9,259,275 B2 | 2/2016 | Burbank |
| 9,259,277 B2 | 2/2016 | Rogers et al. |
| 9,259,281 B2 | 2/2016 | Griffiths et al. |
| 9,259,282 B2 | 2/2016 | Azizian et al. |
| 9,261,172 B2 | 2/2016 | Solomon et al. |
| 9,265,567 B2 | 2/2016 | Orban, III et al. |
| 9,265,584 B2 | 2/2016 | Itkowitz et al. |
| 9,271,633 B2 | 3/2016 | Scott et al. |
| 9,283,049 B2 | 3/2016 | Diolaiti et al. |
| 9,301,811 B2 | 4/2016 | Goldberg et al. |
| 9,314,307 B2 | 4/2016 | Richmond et al. |
| 9,317,651 B2 | 4/2016 | Nixon |
| 9,345,546 B2 | 5/2016 | Toth et al. |
| 9,393,017 B2 | 7/2016 | Flanagan et al. |
| 9,402,689 B2 | 8/2016 | Prisco et al. |
| 9,417,621 B2 | 8/2016 | Diolaiti et al. |
| 9,424,303 B2 | 8/2016 | Hoffman et al. |
| 9,433,418 B2 | 9/2016 | Whitman et al. |
| 9,446,517 B2 | 9/2016 | Burns et al. |
| 9,452,020 B2 | 9/2016 | Griffiths et al. |
| 9,474,569 B2 | 10/2016 | Manzo et al. |
| 9,480,533 B2 | 11/2016 | Devengenzo et al. |
| 9,503,713 B2 | 11/2016 | Zhao et al. |
| 9,550,300 B2 | 1/2017 | Danitz et al. |
| 9,554,859 B2 | 1/2017 | Nowlin et al. |
| 9,566,124 B2 | 2/2017 | Prisco et al. |
| 9,579,164 B2 | 2/2017 | Itkowitz et al. |
| 9,585,641 B2 | 3/2017 | Cooper et al. |
| 9,615,883 B2 | 4/2017 | Schena et al. |
| 9,623,563 B2 | 4/2017 | Nixon |
| 9,623,902 B2 | 4/2017 | Griffiths et al. |
| 9,629,520 B2 | 4/2017 | Diolaiti |
| 9,662,177 B2 | 5/2017 | Weir et al. |
| 9,664,262 B2 | 5/2017 | Donlon et al. |
| 9,687,312 B2 | 6/2017 | Dachs, II et al. |
| 9,700,334 B2 | 7/2017 | Hinman et al. |
| 9,718,190 B2 | 8/2017 | Larkin et al. |
| 9,730,719 B2 | 8/2017 | Brisson et al. |
| 9,737,199 B2 | 8/2017 | Pistor et al. |
| 9,795,446 B2 | 10/2017 | DiMaio et al. |
| 9,797,484 B2 | 10/2017 | Solomon et al. |
| 9,801,690 B2 | 10/2017 | Larkin et al. |
| 9,814,530 B2 | 11/2017 | Weir et al. |
| 9,814,536 B2 | 11/2017 | Goldberg et al. |
| 9,814,537 B2 | 11/2017 | Itkowitz et al. |
| 9,820,823 B2 | 11/2017 | Richmond et al. |
| 9,827,059 B2 | 11/2017 | Robinson et al. |
| 9,830,371 B2 | 11/2017 | Hoffman et al. |
| 9,839,481 B2 | 12/2017 | Blumenkranz et al. |
| 9,839,487 B2 | 12/2017 | Dachs, II |
| 9,850,994 B2 | 12/2017 | Schena |
| 9,855,102 B2 | 1/2018 | Blumenkranz |
| 9,855,107 B2 | 1/2018 | Labonville et al. |
| 9,872,737 B2 | 1/2018 | Nixon |
| 9,877,718 B2 | 1/2018 | Weir et al. |
| 9,883,920 B2 | 2/2018 | Blumenkranz |
| 9,888,974 B2 | 2/2018 | Niemeyer |
| 9,895,813 B2 | 2/2018 | Blumenkranz et al. |
| 9,901,408 B2 | 2/2018 | Larkin |
| 9,918,800 B2 | 3/2018 | Itkowitz et al. |
| 9,943,375 B2 | 4/2018 | Blumenkranz et al. |
| 9,948,852 B2 | 4/2018 | Lilagan et al. |
| 9,949,798 B2 | 4/2018 | Weir |
| 9,949,802 B2 | 4/2018 | Cooper |
| 9,952,107 B2 | 4/2018 | Blumenkranz et al. |
| 9,956,044 B2 | 5/2018 | Gomez et al. |
| 9,980,778 B2 | 5/2018 | Ohline et al. |
| 10,008,017 B2 | 6/2018 | Itkowitz et al. |
| 10,028,793 B2 | 7/2018 | Griffiths et al. |
| 10,033,308 B2 | 7/2018 | Chaghajerdi et al. |
| 10,034,719 B2 | 7/2018 | Richmond et al. |
| 10,052,167 B2 | 8/2018 | Au et al. |
| 10,085,811 B2 | 10/2018 | Weir et al. |
| 10,092,344 B2 | 10/2018 | Mohr et al. |
| 10,123,844 B2 | 11/2018 | Nowlin et al. |
| 10,188,471 B2 | 1/2019 | Brisson |
| 10,201,390 B2 | 2/2019 | Swarup et al. |
| 10,213,202 B2 | 2/2019 | Flanagan et al. |
| 10,258,416 B2 | 4/2019 | Mintz et al. |
| 10,278,782 B2 | 5/2019 | Jarc et al. |
| 10,278,783 B2 | 5/2019 | Itkowitz et al. |
| 10,282,881 B2 | 5/2019 | Itkowitz et al. |
| 10,335,242 B2 | 7/2019 | Devengenzo et al. |
| 10,405,934 B2 | 9/2019 | Prisco et al. |
| 10,433,922 B2 | 10/2019 | Itkowitz et al. |
| 10,464,219 B2 | 11/2019 | Robinson et al. |
| 10,485,621 B2 | 11/2019 | Morrissette et al. |
| 10,500,004 B2 | 12/2019 | Hanuschik et al. |

(56) References Cited

U.S. PATENT DOCUMENTS

| | | |
|---|---|---|
| 10,500,005 B2 | 12/2019 | Weir et al. |
| 10,500,007 B2 | 12/2019 | Richmond et al. |
| 10,507,066 B2 | 12/2019 | DiMaio et al. |
| 10,510,267 B2 | 12/2019 | Jarc et al. |
| 10,524,871 B2 | 1/2020 | Liao |
| 10,548,459 B2 | 2/2020 | Itkowitz et al. |
| 10,575,909 B2 | 3/2020 | Robinson et al. |
| 10,592,529 B2 | 3/2020 | Hoffman et al. |
| 10,595,946 B2 | 3/2020 | Nixon |
| 10,881,469 B2 | 1/2021 | Robinson |
| 10,881,473 B2 | 1/2021 | Itkowitz et al. |
| 10,898,188 B2 | 1/2021 | Burbank |
| 10,898,189 B2 | 1/2021 | McDonald, II |
| 10,905,506 B2 | 2/2021 | Itkowitz et al. |
| 10,912,544 B2 | 2/2021 | Brisson et al. |
| 10,912,619 B2 | 2/2021 | Jarc et al. |
| 10,918,387 B2 | 2/2021 | Duque et al. |
| 10,918,449 B2 | 2/2021 | Solomon et al. |
| 10,932,873 B2 | 3/2021 | Griffiths et al. |
| 10,932,877 B2 | 3/2021 | Devengenzo et al. |
| 10,939,969 B2 | 3/2021 | Swarup et al. |
| 10,939,973 B2 | 3/2021 | DiMaio et al. |
| 10,952,801 B2 | 3/2021 | Miller et al. |
| 10,965,933 B2 | 3/2021 | Jarc |
| 10,966,742 B2 | 4/2021 | Rosa et al. |
| 10,973,517 B2 | 4/2021 | Wixey |
| 10,973,519 B2 | 4/2021 | Weir et al. |
| 10,984,567 B2 | 4/2021 | Itkowitz et al. |
| 10,993,773 B2 | 5/2021 | Cooper et al. |
| 10,993,775 B2 | 5/2021 | Cooper et al. |
| 11,000,331 B2 | 5/2021 | Krom et al. |
| 11,013,567 B2 | 5/2021 | Wu et al. |
| 11,020,138 B2 | 6/2021 | Ragosta |
| 11,020,191 B2 | 6/2021 | Diolaiti et al. |
| 11,020,193 B2 | 6/2021 | Wixey et al. |
| 11,026,755 B2 | 6/2021 | Weir et al. |
| 11,026,759 B2 | 6/2021 | Donlon et al. |
| 11,040,189 B2 | 6/2021 | Vaders et al. |
| 11,045,077 B2 | 6/2021 | Stern et al. |
| 11,045,274 B2 | 6/2021 | Dachs, II et al. |
| 11,058,501 B2 | 7/2021 | Tokarchuk et al. |
| 11,076,925 B2 | 8/2021 | DiMaio et al. |
| 11,090,119 B2 | 8/2021 | Burbank |
| 11,096,687 B2 | 8/2021 | Flanagan et al. |
| 11,098,803 B2 | 8/2021 | Duque et al. |
| 11,109,925 B2 | 9/2021 | Cooper et al. |
| 11,116,578 B2 | 9/2021 | Hoffman et al. |
| 11,129,683 B2 | 9/2021 | Steger et al. |
| 11,135,029 B2 | 10/2021 | Suresh et al. |
| 11,147,552 B2 | 10/2021 | Burbank et al. |
| 11,147,640 B2 | 10/2021 | Jarc et al. |
| 11,154,373 B2 | 10/2021 | Abbott et al. |
| 11,154,374 B2 | 10/2021 | Hanuschik et al. |
| 11,160,622 B2 | 11/2021 | Goldberg et al. |
| 11,160,625 B2 | 11/2021 | Wixey et al. |
| 11,161,243 B2 | 11/2021 | Rabindran et al. |
| 11,166,758 B2 | 11/2021 | Mohr et al. |
| 11,166,770 B2 | 11/2021 | DiMaio et al. |
| 11,166,773 B2 | 11/2021 | Ragosta et al. |
| 11,173,597 B2 | 11/2021 | Rabindran et al. |
| 11,185,378 B2 | 11/2021 | Weir et al. |
| 11,191,596 B2 | 12/2021 | Thompson et al. |
| 11,197,729 B2 | 12/2021 | Thompson et al. |
| 11,213,360 B2 | 1/2022 | Hourtash et al. |
| 11,221,863 B2 | 1/2022 | Azizian et al. |
| 11,234,700 B2 | 2/2022 | Ragosta et al. |
| 11,241,274 B2 | 2/2022 | Vaders et al. |
| 11,241,290 B2 | 2/2022 | Waterbury et al. |
| 11,259,870 B2 | 3/2022 | DiMaio et al. |
| 11,259,884 B2 | 3/2022 | Burbank |
| 11,272,993 B2 | 3/2022 | Gomez et al. |
| 11,272,994 B2 | 3/2022 | Saraliev et al. |
| 11,291,442 B2 | 4/2022 | Wixey et al. |
| 11,291,513 B2 | 4/2022 | Manzo et al. |
| 2008/0039255 A1* | 2/2008 | Jinno ............ A61B 17/29 474/148 |
| 2010/0245549 A1* | 9/2010 | Allen ........... A61B 1/00194 348/E7.001 |
| 2011/0245844 A1* | 10/2011 | Jinno ............ A61B 34/37 606/130 |
| 2014/0025046 A1* | 1/2014 | Williams ...... A61B 17/07207 606/1 |
| 2017/0049298 A1* | 2/2017 | Hunter ......... A61B 1/0055 |
| 2017/0245949 A1* | 8/2017 | Randle ......... B25J 17/0291 |

\* cited by examiner

CAMERA POSITIONING METHOD AND APPARATUS FOR CAPTURING IMAGES DURING A MEDICAL PROCEDURE

CROSS-REFERENCE TO RELATED APPLICATION

This application is a U.S. National Phase Application under 35 U.S.C. 371 of International Application No. PCT/CA2017/000078 filed on Apr. 4, 2017, and published as WO 2017/173524 A1 on Oct. 12, 2017, which claims priority to U.S. Provisional Application No. 62/319,426, filed on Apr. 7, 2016. The entire disclosures of all of the above applications are incorporated herein by reference.

BACKGROUND

1. Field

This disclosure relates generally to positioning a camera for imaging and more particularly to positioning a camera inside a body cavity of a patient for capturing images during a medical procedure.

2. Description of Related Art

Miniaturized cameras are used during investigative medical procedures and surgical procedures such as laparoscopic surgery and computer assisted robotic surgery to produce images of a site of the procedure within a body cavity of the patient. The camera generally includes an illumination source for illuminating the site of the procedure.

SUMMARY

In accordance with one disclosed aspect there is provided an apparatus for positioning a camera to capture images inside a body cavity of a patient during a medical procedure. The apparatus includes an insertion tube, a plurality of connected linkages extending from a distal end of the insertion tube, each linkage having a threaded actuator received on a threaded end of a drive shaft extending between the threaded actuator and a proximal end of the insertion tube. The apparatus also includes a camera disposed at a distal end of the plurality of connected linkages. Each connected linkage has at least one associated movement actuated by movement of the threaded actuator in response to rotation of the drive shaft, the associated movements of the connected linkages together operable to facilitate positioning of the camera within the body cavity of the patient.

Each drive shaft may include a drive coupler at the proximal end of the drive shaft, the drive coupler operable to receive a drive torque for causing rotation of the drive shaft.

The drive couplers may be housed within a drive interface operably configured to removably couple to a driver unit, the driver unit being operable to provide the respective drive torques.

Each drive coupler may include a rotational coupler for transmitting torque to each drive shaft, the rotational coupler being operably configured to receive the proximal end of the drive shaft and to transmit the drive torque to the drive shaft while accommodating linear movement of the proximal end due to resulting movements of the camera.

The rotational coupler may include a tubular body for receiving the proximal end of drive shaft, the tubular body having a slotted portion that engages a pin extending through the proximal end of the drive shaft for coupling to the tubular body.

Each rotational coupler may include a moveable detent coupled to the proximal end of the drive shaft and operable to resiliently engage a fixed detent in the drive interface corresponding to a startup position for each of the proximal ends of the respective drive shafts, the startup positions of the drive shafts defining an insertion position of the camera.

The interface may be removably received on the drive unit, and wherein when received the moveable and fixed detents may be disengaged to permit movement of the camera away from the insertion position. Prior to removal of the interface, the drive unit is operably configured to place the camera in the insertion position causing the moveable and fixed detents to be aligned. When removed, the moveable and fixed detents are engaged to retain the rotational couplers in the startup position.

In the insertion position the camera may be positioned generally in line with a longitudinal axis extending outwardly from the insertion tube.

The plurality of connected linkages may include at least a panning linkage for producing side-to-side motion of the camera, an elevating linkage for moving the camera away from the longitudinal axis, and a tilt linkage for tilting the camera forward and backward with respect to the longitudinal axis.

The panning linkage may be connected to the distal end of the insertion tube, the elevating linkage is connected to the panning linkage and the tilt linkage is connected to the elevating linkage, and the camera may be attached to the tilt linkage.

At least one of the drive shafts may include a compliant portion facilitating bending of the shaft in response to movements of the camera while continuing to permit rotation of the at least one drive shaft.

Each linkage may include a revolute joint constrained to permit motion in a single degree of freedom corresponding to the associated movement of the linkage and the threaded actuator may be coupled to the linkage to cause motion about the revolute joint.

In accordance with another disclosed aspect there is provided a method for positioning a camera to capture images inside a body cavity of a patient during a medical procedure, the camera being disposed at a distal end of a plurality of connected linkages extending from a distal end of an insertion tube, each linkage having a threaded actuator received on a threaded end of a drive shaft extending between the threaded actuator and a proximal end of the insertion tub. The method involves selectively causing rotation of the respective drive shafts to cause movement of the respective threaded actuators, the movement of the respective threaded actuators causing associated movements of the connected linkages to positioning of the camera within the body cavity of the patient.

Selectively causing rotation of the respective drive shafts may involve causing the respective drive shafts to position the camera in an insertion position prior to removal from the body cavity of a patient.

Causing the respective drive shafts to position the camera in an insertion position may involve causing the camera to be positioned generally in line with a longitudinal axis of the insertion tube.

In accordance with another disclosed aspect there is provided an apparatus for positioning a camera to capture images inside a body cavity of a patient during a medical procedure. The apparatus includes an articulated arm includes a plurality of connected moveable linkages, a camera disposed at a distal end of the plurality of connected linkages, the camera including a camera housing enclosing image capture optics, an image sensor, and image capture electronic circuitry operable to produce image data representing images captured by the image sensor, and data transmission electrical circuitry operable to generate and transmit data signals encoding the image data to a host system, the data transmission electrical circuitry being housed within in one of the moveable linkages and coupled to the image capture electronic circuitry via a flexible interconnect.

Other aspects and features will become apparent to those ordinarily skilled in the art upon review of the following description of specific disclosed embodiments in conjunction with the accompanying figures.

BRIEF DESCRIPTION OF THE DRAWINGS

In drawings which illustrate disclosed embodiments.

DETAILED DESCRIPTION

Figure 1:
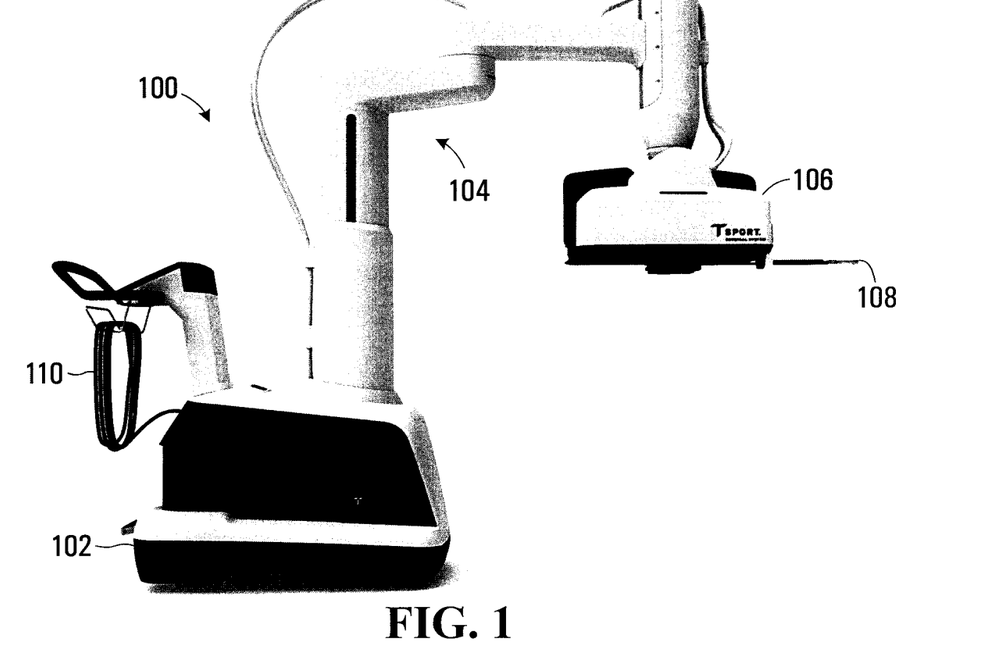
FIG. 1 is a perspective view of a robotic surgical apparatus.

Referring to FIG. 1, a robotic surgical apparatus is shown generally at 100. The surgical apparatus 100 includes a cart 102 that supports an articulated boom 104 that carries a drive unit 106 having a camera 108 mounted on the drive unit. The cart 102 may be wheeled up to a patient (not shown) and the articulated boom 104 deployed to maneuver the drive unit 106 and camera 108 into a location for accessing a body cavity of the patient and positioning a camera to capture images inside the body cavity of a patient during a medical procedure. The surgical apparatus 100 may be controlled by a workstation console (not shown) connected to the surgical apparatus via a cable 110 that carries signals for controlling the drive unit 106 and camera 108.

Figure 2:
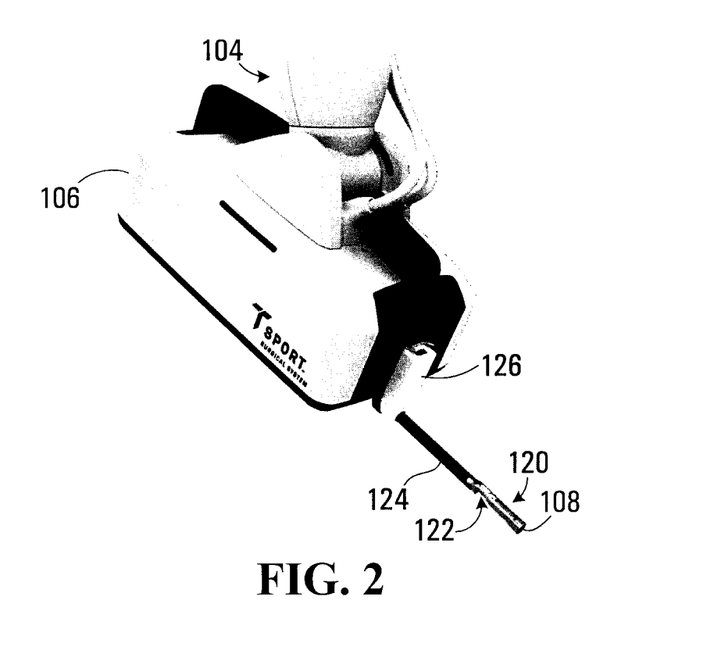
FIG. 2 is a perspective view of a drive unit and camera of the robotic surgical apparatus shown in FIG. 1.

Referring to FIG. 2, the drive unit 106 and camera 108 are shown in front view. The camera 108 is mounted at a distal end of a plurality of connected linkages 120 extending from a distal end 122 of an insertion tube 124. The insertion tube 124 extends outwardly from a drive interface 126 that is removably received on the drive unit 106.

Figures 3, 4:
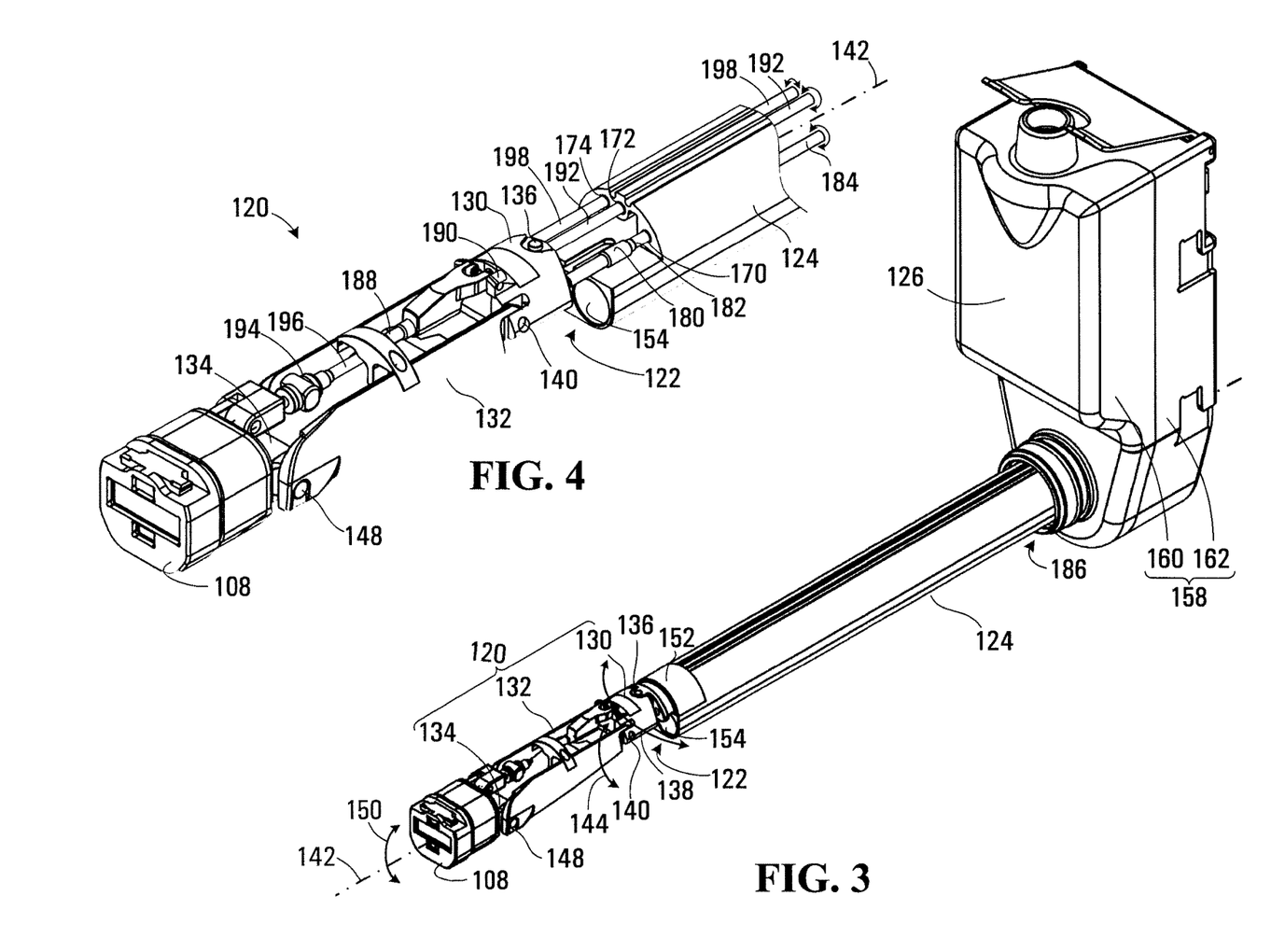
FIG. 3 is a perspective view of an insertion tube, linkages, and the camera shown in FIG. 2.
FIG. 4 is a further enlarged perspective view of the linkages and camera shown in FIG. 3.

The camera 108, insertion tube 124, and drive interface 126 are shown in greater detail in FIG. 3. Referring to FIG. 3, in the embodiment shown the plurality of connected linkages 120 include a panning linkage 130, an elevating linkage 132, and a tilt linkage 134. The panning linkage 130 is connected by a revolute joint 136 to the distal end 122 of the insertion tube 124, which constrains the panning linkage to side-to-side motion in the direction indicated by the arrow 138. The elevating linkage 132 is connected to the panning linkage 130 by a revolute joint 140, which constrains the linkage to movement away from a longitudinal axis 142 in the direction indicated by the arrow 144. The tilt linkage 134 is connected to the elevating linkage 132 by a revolute joint 148, which constrains the linkage to movement for tilting the camera 108 forward and backward with respect to the longitudinal axis 142 in the direction indicated by the arrow 150.

In the embodiment shown the panning linkage 130 is thus connected to the distal end 122 of the insertion tube 124, the elevating linkage 132 is connected to the panning linkage 130 and the tilt linkage 134 is connected to the elevating linkage 132. The camera 108 is disposed at a distal end of the plurality of connected linkages 120, in this case connected to the tilt linkage 134. In other embodiments the plurality of connected linkages 120 may be otherwise arranged and one or more of the linkages may be omitted.

The connected linkages 120 are shown in enlarged detail in FIG. 4 with a distal cap 152 (shown in FIG. 3) on the insertion tube 124 removed. Referring to FIG. 4, the panning linkage 130 has a threaded actuator 180 received on a threaded end 182 of a drive shaft 184. The elevating linkage 132 has a threaded actuator 188 received on a threaded end 190 of a drive shaft 192. The tilt linkage 134 has a threaded actuator 194 received on a threaded end 196 of a drive shaft 198. Each of the drive shafts 184, 192 and 198 extend between the respective threaded actuators 180, 188, and 194 and a proximal end 186 (shown in FIG. 3) of the insertion tube 124. The drive shafts 184, 192 and 198 are routed through respective bores 170, 172, and 174 extending through the insertion tube 124 (only shown in part in FIG. 4). The bores 170, 172, and 174 are sized and configured such that each drive shaft 184, 192 and 198 is freely rotatable within the bores as indicated by the arrows shown in FIG. 4.

Each connected linkage 120 thus has at least one associated movement actuated by movement of the respective threaded actuators 180, 188, and 194 in response to rotation of the respective drive shafts 184, 192 and 198. The associated movements of the connected linkages 120 are together operable to facilitate positioning of the camera 108 within the body cavity of the patient. For example, rotation of the shaft 184 causes the threaded actuator 180 to move either forwardly or rearwardly in a direction aligned with the longitudinal axis 142 causing the panning linkage 130 to pan about the revolute joint 136 moving the camera 108 from side to side. In the embodiment shown, each of the linkages 120 thus includes a revolute joint (136, 140, 148) constrained to permit motion in a single degree of freedom corresponding to the associated movement of the linkage and a threaded actuator (180, 188, and 194) coupled to the linkage to cause motion about the revolute joint.

Figure 5:
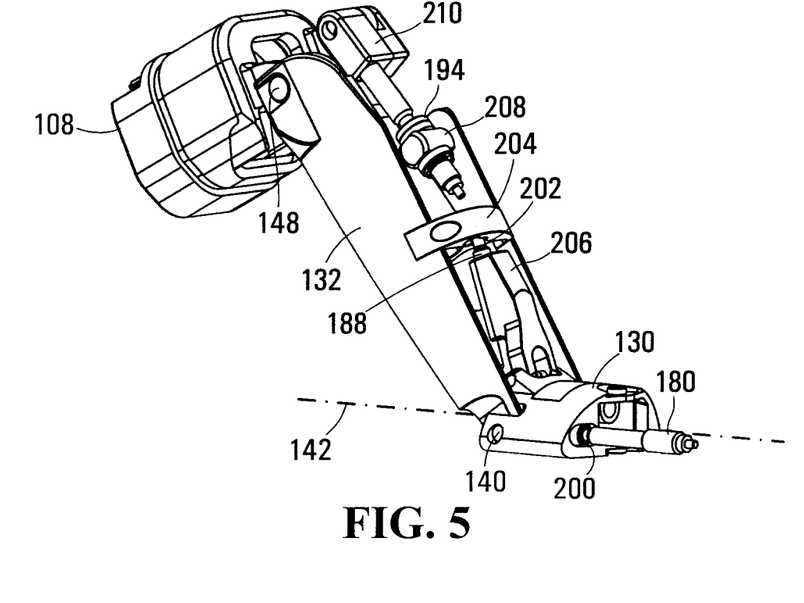
FIG. 5 is a rear perspective view of the linkages and camera in a deployed state.

Referring to FIG. 5, the camera 108 is shown in rear view in a deployed state with the drive shafts 184, 192 and 198 omitted for clarity. The threaded actuator 180 terminates in a ball and socket joint 200 on the rear of the panning linkage 130 which facilitates pivoting at the joint during movement. Similarly the threaded actuator 188 terminates in a ball and socket joint 202 on a strut 204 of the elevating linkage 132. A proximal end threaded actuator 188 is received in a hinged block 206 and rotation of the drive shaft 192 causes the elevating linkage 132 to raise or lower with respect to the longitudinal axis 142. Finally, the threaded actuator 194 is mounted in a first swivel block 208 on the elevating linkage 132 and has a distal end that is clamped to a second swivel block on the tilt linkage 134. Rotation of the drive shaft 198 causes the camera 108 to tilt up or down about the revolute joint 148.

When the drive shafts 184, 192 and 198 are rotated to cause the camera 108 to be deployed, the linkages 120 are displaced from the longitudinal axis 142 causing portions of the drive shafts 192 and 198 running through the panning linkage 130 and elevating linkage 132 to be bent through an angle. The drive shafts 192 and 198 thus have at least a compliant portion within the linkages to facilitating bending of the shaft in response to movements of the camera 108. The compliant portion permits the drive shaft 192 and 198 to be bent through the necessary angle while continuing to permit rotation of the drive shafts for actuating the respective linkages. In some embodiments the drive shafts may be fabricated entirely from a compliant material, while in other embodiments the drive shafts may have some rigid portions and some compliant portions. In one embodiment at least a portion of drive shafts may be fabricated from a hollow stainless steel tube.

Referring back to FIG. 3, the camera 108 and plurality of connected linkages 120 are generally aligned along the longitudinal axis 142 extending outwardly from the insertion tube, which may define an insertion position for inserting the camera 108, linkages 120 and insertion tube 124 into the body cavity of the patient. Once inserted the drive shafts 184, 192 and 198 may be rotated to deploy the camera 108 as shown in FIG. 5. Referring to FIGS. 3 and 4, in the embodiment shown the insertion tube 124 includes at least one bore 154 for receiving an instrument for performing surgical operations within the body cavity of the patient. The instrument may be a dexterous surgical instrument such as described in commonly owned PCT Patent Application PCT/CA2013/001076 entitled ARTICULATED TOOL POSITIONER AND SYSTEM EMPLOYING SAME and PCT Patent Application PCT/CA2015/000098 entitled ACTUATOR AND DRIVE FOR MANIPULATING A TOOL, both of which are incorporated herein in their entirety.

Figure 6:
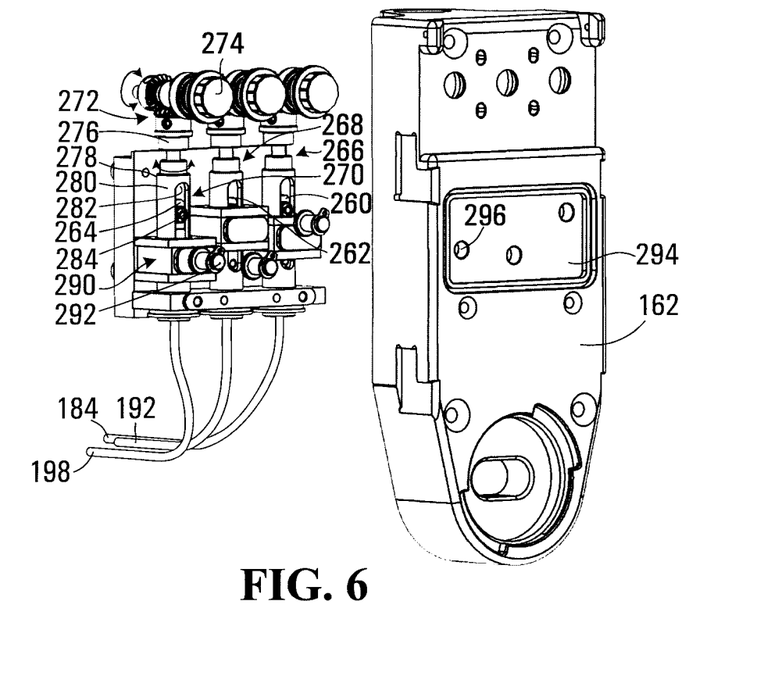
FIG. 6 is a rear perspective view of a drive interface shown in FIG. 3.

Referring back to FIG. 3, the drive interface 126 includes a housing 158 having a front cover 160 and a rear cover 162. Referring to FIG. 6, the drive interface 126 is shown with the front cover 160 omitted and the rear cover 162 removed to reveal the drive components. The drive shafts 184, 192 and 198 are routed back through the respective bores 172, 174, and 176 in the insertion tube 124 and are bent upwardly within the housing 158 and have proximal ends 260, 262, and 264 that terminate in respective drive couplers 266, 268, and 270. The drive couplers 266, 268, and 270 are identical and the drive coupler 270 will be further described herein. The drive coupler 270 includes a bevel gear assembly 272 that receives a drive torque from the drive unit 106 (shown in FIG. 2) at a drive hub 274 when the drive interface 126 is engaged on the drive unit. The bevel gear assembly 272 rotates in the direction indicated by the arrow and the rotating motion is coupled through the gears via a shaft 276 to a rotational coupler 278. The rotational coupler 278 is generally operable to receive the proximal end 264 of the drive shaft 198 and to transmit the drive torque to the drive shaft while accommodating linear movement of the proximal end due to resulting movements of the camera 108. When the plurality of connected linkages 120 move, the drive shafts 184, 192 and 198 extend or retract with the motion, which must be accommodated. In the embodiment shown, the rotational coupler 278 has a tubular body 280 for receiving the proximal end 264 of drive shaft 198. The tubular body 280 has a slotted portion 282 that engages a pin 284 extending through the proximal end of the drive shaft for coupling to the tubular body. The pin 284 couples the rotational torque to the proximal end 264 of the drive shaft 198 while permitting the proximal end and pin to slide within the slotted portion 282 of the tubular body 280, thus accommodating extension or retraction of the drive shaft.

In the embodiment shown the drive coupler 270 also includes a moveable detent mechanism 290, which is coupled to move with the proximal end 264 of the drive shaft 198. The moveable detent 290 has a pin 292 operable to resiliently engage a rear side of a fixed detent plate 294 on the rear cover 162. The fixed detent plate 294 has an opening 296 sized to accommodate a head of the pin 292, the opening being positioned to define a startup position for the proximal end 264 of the drive shaft 198 that places the camera 108 in the insertion position aligned with the longitudinal axis 142, as shown in FIG. 3. In one embodiment, the drive interface 126 is removably received on the drive unit 106 and when received, the pin 292 on the moveable detent mechanism 290 is disengaged to permit movement of the camera 108 away from the insertion position. Prior to removal of the interface 126 from the drive unit 106, the drive unit is operably configured to return the camera 108 to the insertion position causing the pin 292 and the opening 296 on the fixed detent plate 294 to be aligned but not yet engaged. When the drive interface 126 is removed from the drive unit 106, the pin 292 and the opening 296 engage and retain the rotational coupler 278 in the startup position. The drive couplers 266 and 268 have similar moveable and fixed detent mechanisms that operate in the same way. Advantageously, the detent mechanism locks the drive interface 126 in the insertion position when not received on the drive unit 106 preventing movement of the drive hub 274 and other drive hubs which would at least partially deploy the camera 108. The plurality of connected linkages 120 and camera 108 thus remain in the insertion position while being cleaned and sterilized, and when re-used will be in a known orientation.

Figure 7:
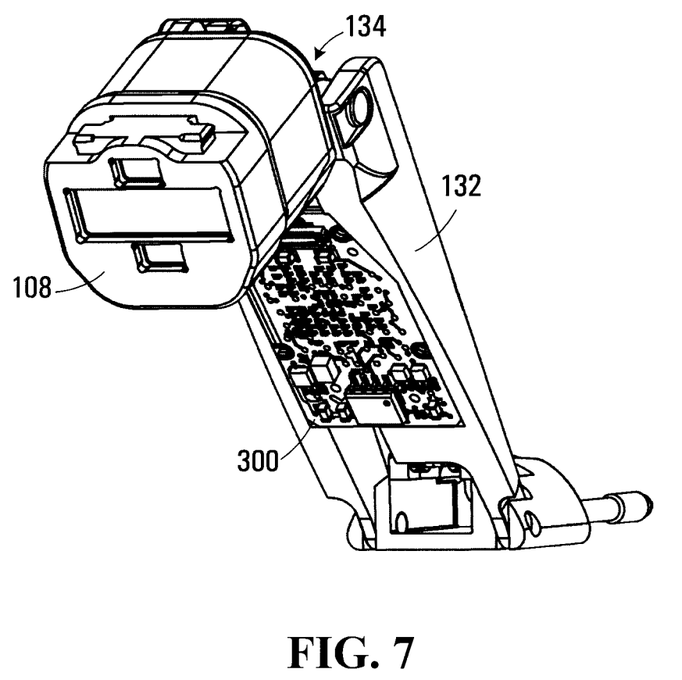
FIG. 7 is a front perspective view of the linkages and camera in a deployed state.

The camera 108 shown in the above embodiments will general be miniaturized to improve access to the body cavity of the patient and to reduce the size of incision needed to provide access for the camera in surgical procedures. In some embodiments, the camera may include one or more high definition image sensors (not shown), where a pair of image sensors are capable of producing stereoscopic 3D views within the body cavity. The image sensors include sensor electronic circuitry that generates image data representing the captured images. The captured image data must be transmitted back to the drive unit 106, which requires additional data transmission circuitry. The image capture electronic circuitry and data transmission electrical circuitry may generate significant heat within the housing of the camera 108. Referring to FIG. 7, in one embodiment the camera 108 houses the image sensors and image capture electronic circuitry. A data transmission printed circuit board 300 carries the data transmission electrical circuitry and is housed within the elevating linkage 132. The image capture electronic circuitry and data transmission electrical circuitry may be coupled via a flexible interconnect (not shown) that permits the 108 to be tilted by the tilt linkage 134. Advantageously, the separation of electrical circuitry places a significant source of heat in the linkage away from the housing of the camera 108, thus spreading the heat load over a larger area.

In accordance with another disclosed aspect there is provided an apparatus for positioning a camera to capture images inside a body cavity of a patient during a medical procedure. The apparatus includes an articulated arm that includes a plurality of connected moveable linkages, a camera disposed at a distal end of the plurality of connected linkages, the camera including a camera housing enclosing image capture optics, an image sensor, and image capture electronic circuitry operable to produce image data representing images captured by the image sensor, and data transmission electrical circuitry operable to generate and transmit data signals encoding the image data to a host system, the data transmission electrical circuitry being housed within in one of the moveable linkages and coupled to the image capture electronic circuitry via a flexible interconnect.

While specific embodiments have been described and illustrated, such embodiments should be considered illustrative of the invention only and not as limiting the invention as construed in accordance with the accompanying claims.

What is claimed is:

1. An apparatus for positioning a camera to capture a plurality of images inside a body cavity of a patient during a medical procedure, the apparatus comprising:
    an insertion tube;
    a plurality of drive shafts extending proximally through the insertion tube, the plurality of drive shafts including:
        a first drive shaft configured to actuate a panning movement of the camera;
        a second drive shaft configured to actuate an elevating movement of the camera; and
        a third drive shaft configured to actuate a tilting movement of the camera;
    a plurality of connected linkages extending from a distal end of the insertion tube, the plurality of connected linkages including:
        a first linkage connected to a distal end of the insertion tube;
        a second linkage connected to the first linkage; and
        a third linkage connected to the second linkage,
        each of the plurality of connected linkages including a threaded actuator received on a threaded end of a respective drive shaft of the plurality of drive shafts, wherein the respective drive shaft of the plurality of drive shafts extend between the threaded actuator and a proximal end of the insertion tube, wherein at least one of the threaded actuators is located distal of at least one of the plurality of connected linkages wherein the threaded actuators include:
        a first threaded actuator received on a threaded end of the first drive shaft such that rotation of the first threaded drive shaft actuates the first threaded actuator to actuate the first linkage of the plurality of linkages to actuate the panning movement of the camera;
        a second threaded actuator received on a threaded end of the second drive shaft such that rotation of the second threaded drive shaft actuates the second threaded actuator to actuate the second linkage of the plurality of linkages to actuate the elevating movement of the camera, wherein the second threaded actuator is located distal of the first threaded actuator; and
        a third threaded actuator received on a threaded end of the third drive shaft such that rotation of the third threaded drive shaft actuates the third threaded actuator to actuate the third linkage of the plurality of linkages to actuate the tilting movement of the camera, wherein the third threaded actuator is located distal of the second threaded actuator;
    a camera disposed at a distal end of the third linkage of the plurality of connected linkages, wherein the camera includes image sensors and image capture electronic circuitry housed within the third linkage; and
    a data transmission printed circuit board housed within the second linkage of the plurality of connected linkages, wherein the data transmission printed circuit board is separated from the image sensors and the image capture electronic circuitry of the camera;
    wherein each linkage of the plurality of connected linkages is configured to move in response to being actuated by movement of the threaded actuator in response to rotation of the respective drive shaft, the associated movements of each linkage of the plurality of the connected linkages together operable to facilitate positioning of the camera within the body cavity of the patient.

2. The apparatus of claim 1 wherein each of the plurality of drive shafts includes a drive coupler at a proximal end of the drive shaft, the drive coupler operable to receive a drive torque for causing rotation of the drive shaft.

3. The apparatus of claim 2 wherein the drive couplers of the plurality of drive shafts are housed within a drive interface operably configured to removably couple to a driver unit, the driver unit being operable to provide the respective drive torques.

4. The apparatus of claim 3 wherein each drive coupler of the plurality of drive shafts comprises a rotational coupler configured to transmit torque to each drive shaft of the plurality of drive shafts, the rotational coupler being operably configured to receive the proximal end of the drive shaft and to transmit the drive torque to the drive shaft while accommodating linear movement of the proximal end of the drive shaft due to resulting movements of the camera.

5. The apparatus of claim 4 wherein at least one rotational coupler comprises a tubular body for receiving the proximal end of drive shaft, the tubular body including a slotted portion that engages a pin extending through the proximal end of the drive shaft and configured to couple to the tubular body.

6. The apparatus of claim 4 wherein each rotational coupler of the plurality of drive shafts includes a moveable detent coupled to the proximal end of the drive shaft and operable to resiliently engage a fixed detent in the drive interface corresponding to a startup position for each of the proximal ends of the respective drive shafts, the startup positions of the drive shafts defining an insertion position of the camera.

7. The apparatus of claim 6 wherein the drive interface is configured to be removably received on a drive unit, and wherein:
    when received, the moveable and fixed detents are disengaged to permit movement of the camera away from the insertion position;
    prior to removal of the drive interface, the drive unit is operably configured to place the camera in the insertion position causing the moveable and fixed detents to be aligned; and
    when removed, the moveable and fixed detents are engaged to retain the rotational couplers in the startup position.

8. The apparatus of claim 6 wherein in the insertion position the camera is positioned generally in line with a longitudinal axis extending outwardly from the insertion tube.

9. The apparatus of claim 1 wherein:
    the first linkage of the plurality of linkages is a panning linkage configured to produce side-to-side motion of the camera;

the second linkage of the plurality of linkages is an elevating linkage configured to move the camera away from the longitudinal axis; and the third linkage of the plurality of linkages is a tilt linkage configured to tilt the camera forward and backward with respect to a longitudinal axis extending outwardly from the insertion tube.

10. The apparatus of claim 1 wherein a drive shaft comprises a compliant portion configured to facilitate bending of the drive shaft in response to movements of the camera while continuing to permit rotation of the drive shaft.

11. The apparatus of claim 1 wherein at least one linkage of the plurality of connected linkages includes a revolute joint constrained to permit motion in a single degree of freedom corresponding to the associated movement of the connected linkage, and wherein the threaded actuator is coupled to the connected linkage to cause motion about the revolute joint.

12. A method for positioning a camera to capture images inside a body cavity of a patient during a medical procedure, the camera being disposed at a distal end of a plurality of connected linkages extending from a distal end of an insertion tube, each of the plurality of connected linkages including a threaded actuator received on a threaded end of a respective drive shaft extending between the threaded actuator and a proximal end of the insertion tube, the method comprising:

providing an apparatus for positioning the camera, the apparatus including:
an insertion tube;
a plurality of drive shafts extending proximally through the insertion tube, the plurality of drive shafts including:
a first drive shaft configured to actuate a panning movement of the camera;
a second drive shaft configured to actuate an elevating movement of the camera; and
a third drive shaft configured to actuate a tilting movement of the camera;
a plurality of connected linkages extending from a distal end of the insertion tube, the plurality of connected linkages including:
a first linkage connected to a distal end of the insertion tube;
a second linkage connected to the first linkage; and
a third linkage connected to the second linkage,
each linkage of the plurality of connected linkages including a threaded actuator received on a threaded end of a respective drive shaft of the plurality of drive shafts, wherein the respective drive shaft of the plurality of drive shafts extend between the threaded actuator and a proximal end of the insertion tube, wherein at least one of the threaded actuators is located distal of at least one of the plurality of connected linkages, wherein the threaded actuators include:
a first threaded actuator received on a threaded end of the first drive shaft such that rotation of the first threaded drive shaft actuates the first threaded actuator to actuate the first linkage of the plurality of linkages to actuate the panning movement of the camera;
a second threaded actuator received on a threaded end of the second drive shaft such that rotation of the second threaded drive shaft actuates the second threaded actuator to actuate the second linkage of the plurality of linkages to actuate the elevating movement of the camera, wherein the second threaded actuator is located distal of the first threaded actuator; and
a third threaded actuator received on a threaded end of the third drive shaft such that rotation of the third threaded drive shaft actuates the third threaded actuator to actuate the third linkage of the plurality of linkages to actuate the tilting movement of the camera, wherein the third threaded actuator is located distal of the second threaded actuator;
the camera disposed at a distal end of the third linkage of the plurality of connected linkages, wherein the camera includes image sensors and image capture electronic circuitry housed within the third linkage; and
a data transmission printed circuit board housed within the second linkage of the plurality of connected linkages, wherein the data transmission printed circuit board is separated from the image sensors and the image capture electronic circuitry of the camera;
selectively causing rotation of at least one of the respective drive shafts to cause movement of the respective threaded actuators, the movement of the respective threaded actuators causing associated movement of the at least one of the plurality of connected linkages to position the camera within the body cavity of the patient.

13. The method of claim 12 wherein selectively causing rotation of at least one of the respective drive shafts comprises causing the respective drive shafts to position the camera in an insertion position prior to removal from the body cavity of a patient.

14. The method of claim 13 wherein causing at least one of the respective drive shafts to position the camera in the insertion position comprises causing the camera to be positioned generally in line with a longitudinal axis of the insertion tube.

15. The method of claim 12, further comprising:
spreading a heat load of the camera between:
image sensors and image capture circuitry of the camera, supported at the distal end of the third linkage of the plurality of linkages; and
the data transmission circuit board disposed in the second linkage of the plurality of linkages.

16. An apparatus for positioning a camera to capture a plurality of images inside a body cavity of a patient during a medical procedure, the apparatus comprising:
an insertion tube;
a plurality of connected linkages extending from a distal end of the insertion tube, at least some of the plurality of connected linkages including a threaded actuator received on a threaded end of a respective drive shaft of a plurality of drive shafts, wherein the respective drive shaft of the plurality of drive shafts extend between the threaded actuator and a proximal end of the insertion tube, wherein at least one of the threaded actuators is located distal of at least one of the plurality of connected linkages;
a camera disposed at a distal end of a distal-most linkage of the plurality of connected linkages, wherein the camera includes image sensors and image capture electronic circuitry housed within the distal-most linkage; and
a data transmission printed circuit board housed within a linkage of the plurality of connected linkages which is proximal of the distal-most linkage, wherein the data transmission printed circuit board is separated from the image sensors and the image capture electronic circuitry of the camera;

wherein at least some of the plurality of connected linkages are configured to move in response to being actuated by movement of the threaded actuator in response to rotation of the respective drive shaft, the associated movements of the at least some of the plurality of the connected linkages together operable to facilitate positioning of the camera within the body cavity of the patient.

17. The apparatus of claim 16 wherein each of the plurality of drive shafts includes a drive coupler at a proximal end of the drive shaft, the drive coupler operable to receive a drive torque for causing rotation of the drive shaft.

18. The apparatus of claim 17 wherein the plurality of connected linkages comprise at least:

a panning linkage configured to produce side-to-side motion of the camera;

an elevating linkage configured to move the camera away from the longitudinal axis; and a tilt linkage configured to tilt the camera forward and backward with respect to a longitudinal axis extending outwardly from the insertion tube.

19. The apparatus of claim 18 wherein the panning linkage is connected to the distal end of the insertion tube, the elevating linkage is connected to the panning linkage and the tilt linkage is connected to the elevating linkage, and wherein the camera is connected to the tilt linkage.

20. The apparatus of claim 16 wherein at least some of the plurality of connected linkages comprise a revolute joint constrained to permit motion in a single degree of freedom corresponding to the associated movement of the connected linkage, and wherein the threaded actuator is coupled to the connected linkage to cause motion about the revolute joint.

* * * * *